United States Patent [19]

Katz

[11] Patent Number: 5,089,268

[45] Date of Patent: Feb. 18, 1992

[54] EGG PHOSPHATIDE LIPID EMULSIONS ALTERED FOR A SPECIFIC THERAPEUTIC FATTY ACID COMPOSITION

[76] Inventor: David P. Katz, 143-30 38th Ave., Flushing, N.Y. 11354

[21] Appl. No.: 642,143

[22] Filed: Jan. 15, 1991

Related U.S. Application Data

[63] Continuation of Ser. No. 518,539, May 2, 1990, abandoned.

[51] Int. Cl.$^5$ .................... A61K 37/22; A61K 31/20; A61E 13/00
[52] U.S. Cl. .................... 424/450; 424/422; 514/560; 514/937; 514/938; 514/943
[58] Field of Search .............. 424/450, 422; 514/937, 514/938, 943, 560

[56] References Cited

U.S. PATENT DOCUMENTS

| | | | |
|---|---|---|---|
| 4,280,996 | 7/1981 | Okamoto et al. | 424/199 |
| 4,678,808 | 7/1987 | Ward et al. | 514/560 |
| 4,820,731 | 4/1989 | Mascioli et al. | 514/549 |

OTHER PUBLICATIONS

Kenshiro Fujimoto et al., Lipid Composition of Tissue and Egg Yolk from Chicken Fed Yeast Grown on N-Paraffins, Poultry Sci., 61, 1015-1018 (1982).

V. K. Tsiagbe et al., Alterations in Phospholipid Composition of Egg Yolks from Laying Hens Fed Choline and Methionine-Supplemented Diets, Poultry Sci. 67, 1717-1724 (1988).

A brochure of KabiVitrum, Inc., Intralipid 20% A 20% I.V. Fat Emulsion (Rev. 8/88).

Primary Examiner—Thurman K. Page
Assistant Examiner—G. S. Kishore
Attorney, Agent, or Firm—Bryan, Cave, McPheeters & McRoberts

[57] ABSTRACT

A sterile lipid emulsion composition made from fish oil enriched egg phosphatides; a natural oil, an osmotic agent such as glycerin and purified water, optionally adjusted to a pH of between 8.5 and 10.5 with sodium hydroxide. This composition can be administered parenterally to a host mammal.

9 Claims, No Drawings

EGG PHOSPHATIDE LIPID EMULSIONS ALTERED FOR A SPECIFIC THERAPEUTIC FATTY ACID COMPOSITION

This is a continuation of U.S. application Ser. No. 07/518,539, filed May 2, 1990 now abandon.

This invention relates to an intravenous lipid emulsion. More particularly, this invention relates to a lipid emulsion derived from egg yolk phosphatides that have been enriched in omega-3 fatty acids.

BACKGROUND OF THE INVENTION

Intravenous lipid emulsions are used as a means of preventing or ameliorating essential fatty acid deficiency in patients who cannot tolerate oral intake. It is also used as a means of providing calories for patients who require parenteral nutrition instead of or as a supplement to oral feeding.

The commercially available sterile lipid emulsion compositions contain triglycerides derived from vegetable oils (neutral lipids) or other sources which represent 10 to 20% (weight/volume) of the lipid emulsions. The additional constituents of the sterile lipid emulsions include glycerin, and, as an emulsifying agent, either soy or egg phosphatides.

Egg yolk phosphatide which is purified in known manner, is the most commonly used emulsifier, although other emulsifiers are also used. These lipid emulsions are made by dispersing the egg yolk phosphatide in warm water using homogenization to create a fine dispersion to which the oil is added.

The conventional oil products used to supply the triglycerides are natural materials such as vegetable and like oils, including butter oil, coconut oil, canola oil, cottonseed oil, lard oil, olive oil, sesame seed oil, soya bean oil, and safflower oil. Soybean oil is preferred due to its ease of purification. These oils are readily accepted by mammals with little or no side effects, but they are primarily rich in fatty acids such as linoleic acid ($C_{18:2}$) which is an omega-6 fatty acid. Linoleic acid is recognized to be an essential fatty acid and necessary for growth and development and the maintenance of normal cell function, since it is a primary constituent of cell membrane. Furthermore it is the precursor for arachidonic acid ($C_{20:4}$) another essential fatty acid, which is the principal precursor for the dienoic prostaglandins, leukotrienes and other hydroperoxy-arachidonate derivatives.

It is known that fish oils are rich in $C_{20-24}$ linear polyunsaturated acids having 5-7 double bonds, which are designated the omega-3 fatty acids. These include the fatty acids eicosapentaenoic acid ($C_{20:5}$) and docosahexaenoic acid ($C_{22:6}$). These acids are also precursors for trienoic prostaglandins and leukotrienes which have a different potency than their omega-6 (dienoic) equivalents. In addition, they are known to have some therapeutic value in treating heart disease, inflammatory disorders, and infection. However, providing large quantities of omega-3 and omega-6 fatty acids in the form of neutral lipids may not be the most optimal form to give to a stressed and/or malnourished patient, given the complexity of the metabolic processes necessary to process the artificial chylomicrons delivered in a sterile lipid emulsion. A more bioavailable form would be useful in treating these patients.

Thus it is desired to provide an improved sterile lipid emulsion that will provide calories and essential fatty acids from both the omega-3 and the omega-6 fatty acids, which, when provided in specific concentrations and combinations, will produce a pharmacological response elicited through the production of eicosanoids, including prostaglandins, leukotrienes and hydroperoxy-arichidonate derivatives.

SUMMARY OF THE INVENTION

An improved sterile lipid emulsion is provided comprising an emulsion of natural oil, fish oil enriched egg yolk phosphatides and glycerin in water. The emulsions of the invention provide both omega-3 and omega-6 fatty acids.

DETAILED DESCRIPTION OF THE INVENTION

Egg yolk phosphatides enriched in omega-3 fatty acids are made by feeding chickens or other egg source diet high in fish oils, particularly eicosapentaenoic acid and decosahexaenoic acid. Fish oils derived from natural fish products, i.e., from cold water ocean fish, particularly those derived from herring, cod, halibut, tuna, sardine, salmon, anchovy and menhaden, are suitable. Certain plant oils are also known to contain high amounts of the omega-3 fatty acids. The resultant egg phosphatides contain from about 10 to 100% higher amounts of the omega-3 fatty acids than products from chickens on conventional diets.

The egg phosphatides are recovered from the egg yolks high in fish oil fatty acids in known manner.

The lipid emulsion compositions of the invention also contain omega-6 fatty acids derived from natural products, such as fish oil, or safflower oil, sunflower oil, soybean oil and the like. Soybean oil has about 53% of omega-6 fatty acids and about 8% of 18 carbon chain length omega-3 fatty acids, whereas safflower oil contains about 78% of omega-6 fatty acids and almost no omega-3 fatty acids. In contrast, fish oils such as menhaden oil have about 22% of omega-3 fatty acids and only 2-6% of omega-6 fatty acids. Thus the relative amounts of oils to be added to the lipid emulsion composition of the invention can be varied depending on the particular oils employed, and the results to be achieved in a particular patient to be treated.

The components of the lipid emulsion compositions of the invention are emulsified in purified, warm water by agitation or other known means.

The preferred compositions of the invention contain from about 1 to about 4% by weight of omega-3 fatty acid enriched egg phosphatides, preferably about 2% by weight, which represents from about 10 to 100% enrichment of omega-3 fatty acids in the egg phosphatides; from about 1 to about 30% by weight, preferably about 2% by weight, of a neutral lipid which may be a mixture of fatty acid triglycerides that contain either or a mixture of omega-3, omega-6 fatty acids and medium chain triglycerides; an osmotic agent such as glycerin in an amount up to about 2.25% by weight, and sterile water to the desired concentration. A basic pH modifier, such as sodium hydroxide, can be added to adjust the pH within the range of 8.5 to 10.5, most preferably from 8.5 to 9.5.

The egg phosphatides are present in finely divided form, preferably in a range of about 0.2 to 1.0 micron particle size. Most preferably the majority of the particles are less than about 0.4 micron in size.

A suitable lipid emulsion composition of the invention contains the following ingredients per liter of emulsion; about 12 milligrams of fish oil enriched egg phosphatides; about 20 milligrams of natural oil such as soybean oil; about 25 milligrams of glycerin (USP grade); and sodium hydroxide added as required to maintain the pH at the desired level.

The lipid emulsion composition is made by warming purified, sterile water to about 50–90 degrees C, while maintaining an inert atmosphere; the recovered fish oil enriched egg phosphatides and the glycerin are added with agitation to disperse the particles, which are prefiltered to pass through an 0.8 micrometer membrane. The dispersion can be carried out in a Manton-Gaulin homogenizer under pressure of about 2000 to 5000 psi in known manner. The resultant mixture is filtered through a 0.45 micrometer membrane and the pH is adjusted with sodium hydroxide solution to within the range of about 8.5 to 10.5. The oil is filtered in like manner, preheated to 50–90 degrees C. and added to the egg phosphatide/glycerin dispersion with agitation. This mixture too can be homogenized as above.

The resultant dispersion is pH adjusted if required, filtered through a membrane having a porosity of 0.8 micrometer or finer, and can be homogenized again. The final lipid emulsion composition is checked for pH in the range of 8.5 to 9.5 and the concentration adjusted with sterile water if required. As is known to one skilled in the art, the emulsion composition of the invention can additionally include other ingredients, including, without limitation, a source of carbohydrates such as dextrose, amino acids, other nutritional supplements such as vitamins, minerals, salts and medications, as indicated.

The resultant emulsion must be maintained in sterile condition and packaged in hermetically sealed containers for short or long term storage. The containers can contain one or more doses of the lipid emulsion composition. The above description is meant to be illustrative only of the present invention, and not limiting thereof. Other variations of composition and manufacture are well known to those skilled in the art and are meant to be included herein.

We claim:

1. In a sterile lipid emulsion for parenteral use, comprising:
    (a) from 1 to 30% by weight of a neutral lipid mixture of fatty acid triglycerides containing omega-3 fatty acids, omega-6 fatty acids, medium chain length triglycerides or mixtures thereof;
    (b) from 1 to 4% by weight of an egg yolk phosphatide emulsifier;
    (c) up to 2.25% by weight of an osmolality modifier; and
    (d) sterile water;
    the improvement, wherein the egg yolk phosphatide is derived from the eggs of chickens whose diets have been supplemented with fish oils which are rich in eicosapentaenoic acid, docosahexaenoic acid or mixtures thereof, said egg yolk phosphatide containing from 10 to 100% higher amounts of omega-3 fatty acids than egg yolk phosphatides derived from the eggs of chickens whose diets have not been so supplemented.

2. The sterile lipid emulsion of claim 1, wherein the neutral lipid mixture is derived from at least one natural oil selected from the group consisting of fish oil, butter oil, coconut oil, cottonseed oil, lard, olive oil, sesame seed oil, soya bean oil, safflower oil and sunflower oil.

3. The sterile lipid emulsion of claim 2, wherein the natural oil is soybean oil.

4. The sterile lipid emulsion of claim 1, wherein the egg yolk phosphatide emulsifier is derived from the eggs of chickens whose diets have been supplemented with at least one fish oil selected from the group consisting of herring, cod, halibut, tuna, sardine, salmon, anchovy or menhaden oils.

5. The sterile lipid emulsion of claim 1, whose pH has been adjusted with base to a pH of from 8.5 to 10.5.

6. The sterile lipid emulsion of claim 1, wherein said osmolality modifier is glycerin.

7. In a sterile lipid emulsion for parenteral use, comprising:
    (a) from 1 to 30% by weight of soybean oil;
    (b) from 1 to 4% by weight of finely divided particles of an egg yolk phosphatide emulsifier;
    (c) up to 2.25% by weight of glycerin as an osmolality modifier;
    (d) sterile water; and
    (e) a basic pH modifier in an amount sufficient to adjust the pH of the emulsion to a pH of from 8.5 to 10.5;
    the improvement, wherein the egg yolk phosphatide is derived from the eggs of chickens whose diets have been supplemented with at least one fish oil selected from the group consisting of herring, code, one or more of the fish oils derived from herring, cod, halibut, tuna, sardine, salmon, anchovy or menhaden oil, said egg yolk phosphatide containing from 10 to 100% higher amounts of omega-3 fatty acids than egg yolk phosphatides derived from the eggs of chickens whose diets have not been so supplemented.

8. The sterile lipid emulsion of claim 7, wherein the egg yolk phosphatide emulsifier particles are within the range of from 0.2 to 1.0 micron in size.

9. The sterile lipid emulsion of claim 7, containing:
    (a) 2% by weight soybean oil;
    (b) 2% by weight of the egg yolk phosphatide emulsifier; and
    (c) sodium hydroxide in an amount sufficient to adjust the pH of the emulsion to from 8.5 to 9.5.

* * * * *

UNITED STATES PATENT AND TRADEMARK OFFICE
CERTIFICATE OF CORRECTION

PATENT NO. : 5,089,268
DATED : February 18, 1992
INVENTOR(S): DAVID P. KATZ

It is certified that error appears in the above-identified patent and that said Letters Patent is hereby corrected as shown below:

Column 2, line 18: After "source", insert --a--.

Column 3, line 18: After "C", delete --.--.

Claim 7, column 4, lines 38-40: After "herring," delete --code, one or more of the fish oil derived from herring--.

Signed and Sealed this

Twenty-sixth Day of October, 1993

Attest:

BRUCE LEHMAN

Attesting Officer

Commissioner of Patents and Trademarks